(12) United States Patent
Dutzig et al.

(10) Patent No.: US 9,809,364 B2
(45) Date of Patent: Nov. 7, 2017

(54) PACKAGED RODENTICIDAL BAIT

(71) Applicant: BASF Agro B.V., EA Arnhem (NL)

(72) Inventors: Holger Dutzig, Rheinzabern (DE); Sharon Hughes, Widnes (GB)

(73) Assignee: BASF Agro B.V., Arnhem (NL)

(*) Notice: Subject to any disclaimer, the term of this patent is extended or adjusted under 35 U.S.C. 154(b) by 0 days.

(21) Appl. No.: 14/888,246

(22) PCT Filed: Apr. 24, 2014

(86) PCT No.: PCT/EP2014/058329
§ 371 (c)(1),
(2) Date: Oct. 30, 2015

(87) PCT Pub. No.: WO2014/177449
PCT Pub. Date: Nov. 6, 2014

(65) Prior Publication Data
US 2016/0075493 A1    Mar. 17, 2016

(30) Foreign Application Priority Data

May 2, 2013  (EP) .................................... 13166319
Jan. 27, 2014 (EP) .................................... 14152619

(51) Int. Cl.
| | |
|---|---|
| *B65D 65/38* | (2006.01) |
| *A01N 25/00* | (2006.01) |
| *A01N 31/06* | (2006.01) |
| *B65B 51/10* | (2006.01) |
| *B65D 75/00* | (2006.01) |
| *B65D 75/30* | (2006.01) |
| *B65D 85/00* | (2006.01) |

(52) U.S. Cl.
CPC ........... *B65D 65/38* (2013.01); *A01N 25/004* (2013.01); *A01N 31/06* (2013.01); *B65B 51/10* (2013.01); *B65D 75/002* (2013.01); *B65D 75/30* (2013.01); *B65D 85/70* (2013.01)

(58) Field of Classification Search
None
See application file for complete search history.

(56) References Cited

U.S. PATENT DOCUMENTS 4,485,133 A * 11/1984 Ohtsuka ................. B32B 27/12
206/0.7

FOREIGN PATENT DOCUMENTS

| | | |
|---|---|---|
| EP | 1279334 A1 | 1/2003 |
| EP | 2153719 A1 | 2/2010 |
| FR | 2037769 A5 | 12/1970 |
| FR | 2505251 A1 | 11/1982 |
| GB | 2014454 A1 | 8/1979 |
| WO | 14064272 A1 | 5/2014 |
| WO | 14154621 A1 | 10/2014 |

OTHER PUBLICATIONS

Dubock (GB 2014454 A).*
Flatres (EP 2153719 A1).*
FR 2037769 English translation.*
International Search Report, issued in PCT/EP2014/058329, dated May 27, 2014.
International Preliminary Report on Patentability, issued in PCT/EP2014/058329, dated Oct. 2, 2015.

* cited by examiner

*Primary Examiner* — Robert A Wax
*Assistant Examiner* — Quanglong Truong
(74) *Attorney, Agent, or Firm* — Brinks Gilson & Lione

(57) ABSTRACT

A packaged rodenticidal bait comprises a soft bait composition enrobed in a perforated thermoplastic film, wherein the soft bait composition comprises a blend of at least one edible fat, at least one particulate food component and at least one rodenticidally-active substance. Preferably, the thermoplastic film comprises one or more polyolefins.

The perforated film used in the manufacture of the packaged bait according to the invention does not absorb fat, unlike conventionally-used paper sachets. The packaged bait composition of the invention is palatable to rodents such that rodents may take a lethal dose of a rodenticide from the bait in a single sitting.

19 Claims, No Drawings

PACKAGED RODENTICIDAL BAIT

This application is a National Stage application of International Application No. PCT/EP2014/058329, filed Apr. 24, 2014. This application also claims priority under 35 U.S.C. §119 to European Patent Application No. 13166319.7, filed May 2, 2013, and to European Patent Application No. 14152619.4, filed Jan. 27, 2014.

The present invention relates to packaged rodenticidal bait. More particularly, it relates to packaged soft bait compositions for use in the control of rodents, particularly rats and mice.

Baits containing a rodenticidally-active substance are often formulated as soft, paste-like compositions. These soft bait compositions typically contain a blend of a particulate food component, such as cereal flour, with a fat, which acts as a binder for the particulate component as well as a feeding stimulant for the rodent, which blend contains one or more rodenticidally-active substances. The use of the fat in the composition provides a blend which is capable of being divided into small quantities and moulded or shaped.

Conventionally, soft bait compositions are packaged, for single feed application, in paper sachets. The paper sachets keep the bait contained and uncontaminated until consumption by the rodent and allow the bait to be stored and to be placed in suitable locations for rodent control in an easy-to-use manner by both professional users and general public users alike. The walls of such sachets allow the aromas from the constituents of the composition to pass so as to attract rodents to the bait.

Paper sachets are absorbent and, thus, absorb fat from the soft bait composition. Absorption of fat is exacerbated during warm environmental conditions when the fat component in the soft bait composition softens as it begins to melt. The absorption of fat by the paper sachet has the effect of bringing fat to the surface of the bait which, unfortunately, detracts from the palatability of the bait for the target rodent. Furthermore, many rodenticidally-active substances used in baits for rodent control are lipophilic. In such circumstances, therefore, the fat absorbed into a paper sachet contains fat-soluble rodenticidally-active substance. The bringing of fat and fat-soluble active substance to the surface of the bait in this way reduces palatability and clearly undermines the concept of manufacturing a blend which is palatable to rodents. Furthermore, a paper sachet containing absorbed fat and fat-soluble rodenticide increases the risk that rats become bait-shy and do not take a lethal dose of the rodenticide from the bait in a single sitting.

The object of the present invention is to provide a packaged bait which overcomes the problems associated with conventional paper sachet-contained soft bait compositions.

According to the present invention, there is provided a packaged rodenticidal bait comprising a non-particulate soft bait composition enrobed in a perforated thermoplastic film wherein the soft bait composition comprises a blend of at least one edible fat, at least one particulate food component and at least one rodenticidally-active substance.

By the term "enrobed", as used herein, we mean that the soft bait composition is closely wrapped in the perforated thermoplastic film such that it is not loosely contained therein. Preferably, the soft bait composition is tightly enclosed within the perforated thermoplastic film.

By the expression "soft bait composition" we mean a bait composition that is formulated so as to have a paste-like consistency, i.e. to yield readily to touch or pressure and be deformable. Preferably, the soft bait composition has the property of plasticity.

The packaged bait according to the present invention overcomes the problems associated with baits packaged in paper sachets since it does not suffer from fat absorption by the perforated thermoplastic film and, thus, fat transport to the surface yet it still allows aromas to escape the film to act as attractants to rodents.

The soft bait composition, according to the present invention, is enrobed in a perforated thermoplastic film. Preferably, the thermoplastic film comprises one or more polyolefins, typically selected from polyethylene, polypropylene and copolymers of ethylene and polypropylene.

The thermoplastic film may be a monolayer film or a multi-layer film. Multi-layer polyolefin films are well-known in the art and typically comprise a "core" layer and a "skin" layer on each side of the "core" layer. The "core" layer may comprise a polymeric blend, the major constituent of which blend being either a homopolymer or copolymer of ethylene and a minor constituent being either a homopolymer or copolymer of butylene. The "skin" layers typically comprise a homopolymer of ethylene or of propylene or a copolymer of ethylene and propylene. Preferably, the film, whether a monolayer film or a multi-layer film, is oriented so that it is heat-shrinkable in at least one direction. The use of a shrink film makes it possible to shrink the film around the bait composition so that the bait composition is tightly enclosed or wrapped within the film.

Thermoplastic films are commercially available in a variety of film thicknesses. Typical thickness ranges from 13 to 25 μm. We have found that packaged baits manufactured using perforated polyolefin film having a film thickness of 19 μm have good palatability characteristics for rodents. Films having a thickness of 25 μm are acceptable but have a lower palatability for rats compared to films of 19 μm thickness.

The thermoplastic film used in the manufacture of the packaged rodenticidal bait of the invention is perforated. Pre-perforated films are well known in the art. The perforations in the film allow aromas, from the bait composition, to escape so that they act as feeding stimulants for the target rodents and, thus, increase the palatability of the bait. The hole diameters are, however, too small to allow the bait composition or components thereof to escape. By the term "perforations" we mean a plurality of deliberately-created small holes in the film. The perforations are preferably provided in the film forming the walls of the packaged bait in a uniform manner, i.e. each perforation is spaced substantially equidistant from its neighbouring holes, so as to optimise the escape of aroma from the packaged bait. Typically, the perforated thermoplastic film contains 100 to 300 perforations per square decimeter, preferably from 150 to 250 perforations per square decimeter. We have found that the use of a multi-layer coextruded polyolefin shrink film having a uniform perforation of about 200 perforations per square decimeter enables the manufacture of a packaged bait which has excellent performance in allowing aroma escape and, therefore, ensuring good palatability for rodents. The perforated thermoplastic film used in the present invention will have good resistance to wear and tear and have good resistance to environmental conditions of heat and light. Such perforated thermoplastic films are easily available commercially.

The soft bait composition used in the manufacture of the packaged bait comprises a blend of at least one edible fat, at least one particulate food component and at least one rodenticidally-active substance.

The edible fat may be an animal fat or a vegetable fat or may be a combination of animal and vegetable fats. According to one embodiment, the edible fat may be one which is not completely liquid at a temperature of 35° C. By the expression "not completely liquid", we mean that the edible fat comprises solid fat crystals in addition to any liquid oils. Thus, according to this embodiment, the edible fat is solid at normal room temperature (20° C.) but is not completely melted at a temperature of 35° C. An example of a vegetable fat which meets this preferred requirement is refined palm oil, a fat which is particularly palatable to rodents.

The soft bait composition, which itself is non-particulate, contains at least one particulate food component. Preferably, the particulate food component comprises a vegetable flour which may be a cereal flour, a non-cereal flour or a mixture of both cereal and non-cereal flours. Examples of cereal flours include oat flour, wheat flour, rice flour and maize flour. Examples of non-cereal flours include potato flour, peanut flour and soy flour. Mixtures of any two or more of these flours may be used in the particulate food component of the bait.

The particulate food component of the bait may also comprise one or more whole grains, nuts or seeds, ground grains, nuts or seeds or comminuted grains, nuts or seeds or any mixture of such. Preferably, the particulate food component will contain one or more of pinhead oatmeal, cut wheat, corn grits, canary seed, poppy seed, sesame seed and sunflower seed.

The soft bait composition used in the manufacture of the present invention is formulated so as to have a paste-like consistency. Typically, it comprises a mixture of the fat and particulate food components in the form of a paste. By the term "paste" used herein, we mean a soft, viscous material comprising a dispersion of fine particulate solids in fat which is capable of being moulded or shaped. It will be apparent to the person skilled in the art that the weight ratio of edible fat:particulate food composition used in the soft bait composition will be such that the composition has a paste-like consistency, i.e. it has the characteristic of being deformable. Too much fat or oil which is liquid at ambient temperature will result in a composition that is runny whereas not enough fat or oil will result in a composition that is too unyielding under pressure and, therefore, a composition that does not have a paste-like consistency. Typically, the amount of edible fat in the soft bait composition will be in the range of from 5 to 30% by weight based on the total weight of the composition. Preferably, the soft bait composition comprises at least 7.5%, more preferably at least 10%, by weight of edible fat based on the total weight of the composition. Preferably, the soft bait composition comprises not greater than 25%, more preferably not greater than 20% and most preferably not greater than 18%, by weight of edible fat based on the total weight of the composition.

The soft bait composition of the invention contains at least one rodenticidally-active substance. The rodenticidally-active substance may be an anticoagulant rodenticide, a non-anticoagulant rodenticide or a natural or synthetic poison. Examples of suitable anticoagulant rodenticides include difenacoum, flocoumafen, brodifacoum, bromodiolone, diphacinone, difethialone, warfarin, sodium warfarin, coumatetralyl, chlorophacinone, coumachlor, coumafuryl and pindone. Examples of non-anticoagulant rodenticides include vitamin D, for instance cholecalciferol (vitamin D3), ergocalciferol (vitamin D2) and norbormide. Other rodenticides that may be used in the present invention include natural poisons, such as strychnine and scilliroside, as well as synthetic poisons such as metal phosphides, for example zinc phosphide, sodium monofluoroacetate and metal cyanides, for example sodium cyanide, and α-chloralose.

Microencapsulated forms of the rodenticidally-active substance may also be used in the composition of the present invention.

According to a preferred embodiment, the soft bait composition of the present invention contains a non-anticoagulant rodenticide and, more preferably, cholecalciferol. We have found that cholecalciferol is sufficiently toxic to rats and mice and is effective against anticoagulant-resistant rodents.

Typically, an anticoagulant rodenticide will be used in an amount in the range of from 0.001 to 0.05% by weight, preferably 0.001 to 0.025%, and more preferably 0.0025 to 0.025%, by weight based on the total weight of the bait composition. If the bait contains vitamin D as the rodenticidally-active substance, this will typically be used in an amount of 250-10000 ppm (0.025-1.0% by weight based on the total weight of the bait). The actual amount used will, of course, depend on the identity of the rodenticidally-active substance used and on the target pest.

The soft bait composition of the present invention may, advantageously, also contain one or more components such as sweetening agents, vegetable oil, additional food components, pigments or dyes, flavouring agents, preservatives, antioxidants and taste deterrents. Such additional components are well known to the person skilled in the art.

Preferably, the soft bait composition contains a sweetening agent. Typically, the sweetening agent is sucrose, preferably icing sugar.

Although palm oil and icing sugar in the soft bait composition provide flavours which are very attractive to rodents, it may further be desired to include one or more additional agents which provide extra flavours and/or aromas to the soft bait composition to increase yet further the palatability of the composition.

It is conventional, in the art of rodenticides, to include one or more substances which act as a deterrent to humans. Such substances typically provide a flavour and/or aroma which is repellent to humans. Typical of such substances are bittering substances which give a bait an unpleasant taste noticeable by humans. An example of such a taste deterrent is denatonium benzoate. Such deterrent substances may be included in a total amount which is typically about 0.001% by weight based on the total weight of the soft bait composition.

The soft bait composition will typically be coloured, by the incorporation of a colorant, e.g. a dye or pigment, to aid identification. Typically, a colorant will be present in an amount of about 0.002% by weight based on the total weight of the composition.

The invention also relates to a method of manufacturing the packaged rodenticidal bait described herein. The method comprises the steps:
(i) providing a soft bait composition on a sheet of perforated thermoplastic film;
(ii) folding the sheet of perforated thermoplastic film such that an upper portion of the film overlies a lower portion of the film and the soft bait composition is located between the upper portion and the lower portion of the folded sheet of film; and
(iii) heat-sealing together the upper portion of the film with the lower portion of the film where the upper portion contacts the lower portion so as to enrobe the soft bait composition in the film.

Typically, the packaged rodenticidal bait will be manufactured for utility as a single feed application. For convenience of use, therefore, the perforated thermoplastic film may be cut to dimensions such that a packaged bait will be approximately 6 cm by 7 cm. Such a size of packaged bait can accommodate sufficient bait composition that will be formulated not only for optimum palatability but also to deliver a lethal dose of rodenticidally-active substance to a rodent at a single sitting.

EXAMPLE

1. A five-layer coextruded polyolefin shrink film, pre-perforated at a perforation density of 200 per square decimeter, was used to manufacture a packaged rodenticidal bait according to the present invention.

A soft bait composition having the formulation shown in the Table below was prepared according to conventional methods.

TABLE

| Ingredient | Amount (g) |
| --- | --- |
| Cholecalciferol | 0.075 |
| denatonium benzoate | 0.001 |
| oils and fats | 14.5 |
| sugar | 10.0 |
| inerts and colourant | 1.0 |
| vegetable flour and edible seeds/grains | balance to 100 g |

100 g of the soft bait composition was placed on a 6 cm×14 cm sheet of the pre-perforated polyolefin film. The film was folded, lengthwise, over the bait composition with the three free edges of each of top and bottom portions of the film superimposed. The superimposed top and bottom portions of the film were heat-sealed together to make a packaged bait wherein the bait composition is enrobed in the polyolefin film.

2. Packaged baits, according to the invention, prepared in accordance with the above-described procedure were used in a field trial as described below. For comparison, conventional paper sachets containing the soft bait composition having the formulation shown in the above Table were prepared and used in the field trial.

In accordance with standard procedure, suitable trial sites, each having an identified infestation of mice (*Mus domesticus*) were selected and baiting locations in the mouse runs were identified. Tracking activity for the mice was measured over 4 days prior to each trial (pre-census) and for 4 days post trial (post-census). Non-poisoned bait was used for the pre-trial census and post-trial census periods and the poisoned bait, as described above, was used for the trial period itself which lasted 21 days. Bait take by the mice, over these periods, was regularly measured. In one trial, the bait composition described above and packaged in paper sachets was used. In the other trial, the bait composition described above enrobed in pre-perforated polyolefin film, as described above, was used.

For the trial using the paper sacheted bait composition, tracking scores indicated that no reduction in mouse population had occurred and bait take was low. It was calculated from the tracking scores and the bait take measurement that 0% control was achieved over the trial period using the bait composition packaged in paper sachets.

For the trial using the bait composition enrobed in the polyolefin film, tracking scores dropped sharply over the 21 day trial period. Over the same period, take dropped from over 300 g (in the pre-trial census period) to about 15 g on day 21. It was calculated from the tracking scores and the census take measurements that 92% control had been achieved over the trial period using the bait composition enrobed in the polyolefin film.

The results of these trials indicate that the mice in the field trials found the paper sacheted composition to be unattractive whereas the polyolefin film-enrobed composition was highly palatable to the mice.

3. Polyolefin film-enrobed bait composition prepared as described in 1. above and conventional paper sachets containing the soft bait composition having the formulation shown in the above table, as described in 2. above, were heat-treated for 24 hours in an oven at a temperature of 54° C. Following this heat treatment, the polyolefin film-enrobed bait composition and the paper sachets were allowed to cool to ambient temperature and each was used as test bait in the following test procedure.

Test Procedure

The test bait and an alternative control (containing no active substance) were offered to each of five male Wistar Rats. The alternative control used in the test was LabDiet (Registered Trade Mark) EURodent Diet 22% 5LFS from PMI Nutrition International. The ingredient composition of this diet is:

| cereal products (corn, wheat, wheat middlings) | 58.2% |
| --- | --- |
| vegetable proteins (dehulled soybean meal, dehydrated alfafa, dried beet pulp, dried brewers yeast) | 37.2% |
| energy sources (soybean oil) | 1.75% |
| supplementation (vitamins, major minerals, trace minerals, amino acids) | 2.85% |

The total test bait and control diet for all five animals were summed and the palatability ratio for each test bait was calculated as follows:

$$\text{Palatability Ratio (group of five animals)} = \frac{\text{Total test bait take (g)}}{\text{Total control diet take (g)}}$$

Thus, a palatability ratio of >1.0 indicates that the test bait was more palatable to the rats than the control diet whereas a palatability ratio of 1.0 indicates that the test bait and the control diet were equally palatable.

The palatability ratio obtained for the heat-treated, packaged bait of the invention was 4.51. Compared to this, the palatability ratio obtained for the heat-treated paper sachet containing the bait formulation shown in the table was 3.51. The result of the test can be explained by the fact that the conventional paper sachets absorb fat which is released from the bait formulation during the heat treatment and that the fat absorbed into the paper sachet reduces palatability of the packaged bait. Although the difference between these palatability ratios is not a significant one, the results indicate a trend which is expected to be mirrored in the field.

The invention claimed is:

1. A packaged rodenticidal bait comprising a non-particulate soft bait composition enrobed in a perforated thermoplastic film, wherein the soft bait composition comprises a blend of at least one edible fat, at least one particulate food component and at least one rodenticidally-active substance.

2. The packaged rodenticidal bait of claim 1, wherein the perforated thermoplastic film comprises one or more polyolefins.

3. The packaged rodenticidal bait of claim 2, wherein the perforated thermoplastic film comprises a polyolefin selected from polyethylene, polypropylene and copolymers of ethylene and propylene.

4. The packaged rodenticidal bait of claim 1, wherein the thermoplastic film is a monolayer film.

5. The packaged rodenticidal bait claim 1, wherein the thermoplastic film is a multi-layer film.

6. The packaged rodenticidal bait of claim 1, wherein the thermoplastic film is a shrink film.

7. The packaged rodenticidal bait of claim 1, wherein the perforated thermoplastic film contains from 100 to 300 perforations per square decimeter.

8. The packaged rodenticidal bait of claim 7, wherein the perforated thermoplastic film contains from 150 to 250 perforations per square decimeter.

9. The packaged rodenticidal bait of claim 1, wherein the thermoplastic film has a thickness of from 15 to 25 μm.

10. The packaged rodenticidal bait of claim 9, wherein the thermoplastic film has a thickness of from 18 to 20 μm.

11. The packaged rodenticidal bait of claim 1, wherein the soft bait composition contains a fat which is not completely liquid at a temperature of 35° C.

12. The packaged rodenticidal bait of claim 1, wherein the fat is an animal fat, a vegetable fat or a mixture thereof.

13. The packaged rodenticidal bait of claim 12, wherein the fat is refined palm oil.

14. The packaged rodenticidal bait of claim 1, wherein the soft bait composition contains at least one particulate food component which is a vegetable flour selected from cereal flour and non-cereal flour.

15. The packaged rodenticidal bait of claim 14, wherein the vegetable flour is selected from the group consisting of oat flour, wheat flour, rice flour, maize flour, potato flour, peanut flour and soy flour and combinations thereof.

16. The packaged rodenticidal bait of claim 1, wherein the soft bait composition contains one or more whole grains or seeds, ground grains or seeds, cut or comminuted grains or seeds and combinations thereof.

17. The packaged rodenticidal bait of claim 16, wherein the soft bait composition contains one or more of pinhead oatmeal, cut wheat, corn grits, canary seed, poppy seed, sesame seed and sunflower seed.

18. The packaged rodenticidal bait of claim 1, wherein the rodenticidally-active substance is selected from the group consisting of difenacoum, brodifacoum, flocoumafen, bromodiolone, difethialone, warfarin, coumatetralyl, chlorophacinone, diphacinone, coumachlor, coumafuryl, pindone, ergocalciferol, cholecalciferol, norbormide, alphachloralose, strychnine, sodium monofluoroacetate and sodium cyanide.

19. A method of manufacturing the packaged rodenticidal bait of claim 1, comprising the steps of:
 (i) providing a soft bait composition on a sheet of perforated thermoplastic film;
 (ii) folding the sheet of perforated thermoplastic film such that an upper portion of the film overlies a lower portion of the film and the soft bait composition is located between the upper portion and the lower portion of the folded sheet of film; and
 (iii) heat-sealing together the upper portion of the film with the lower portion of the film where the upper portion contacts the lower portion so as to enrobe the soft bait composition in the film.

\* \* \* \* \*